United States Patent [19]

Glovsky et al.

[11] 3,966,896
[45] June 29, 1976

[54] RADIOIMMUNOASSAY FOR PLASMA RENIN ACTIVITY

[75] Inventors: Joel Glovsky, Fenton; James L. Brown, House Springs, both of Mo.

[73] Assignee: Mallinckrodt, Inc., St. Louis, Mo.

[22] Filed: Sept. 6, 1974

[21] Appl. No.: 503,648

[52] U.S. Cl. .............................. 195/103.7; 23/230 B
[51] Int. Cl.² .................. A61K 43/00; G01T 1/16; G01N 33/00
[58] Field of Search ............... 424/1, 1.5; 23/230 B, 23/259; 195/103.5

[56] References Cited
UNITED STATES PATENTS

| | | | |
|---|---|---|---|
| 3,592,888 | 7/1971 | Wolf | 424/1 |
| 3,889,298 | 8/1975 | Szczesniak | 424/1 X |

*Primary Examiner*—Leland A. Sebastian
*Assistant Examiner*—Christine M. Nucker
*Attorney, Agent, or Firm*—Koenig, Senniger, Powers and Leavitt

[57] ABSTRACT

A radioimmunoassay method for the in vitro determination of the renin activity of an unknown plasma sample. In this method an unknown generation sample is provided by mixing the unknown plasma sample with a generation buffer solution and an inhibitor for enzymes which convert angiotensin I to other substances. The unknown generation sample is incubated to generate angiotensin I therein by action of renin upon angiotensinogen, thereby producing a generated unknown sample. A generated unknown radioimmunoassay reaction mixture is provided by mixing the generated unknown plasma sample with a predetermined amount of radioactively labeled angiotensin I, a predetermined amount of an antibody for angiotensin I, and an amount of an assay buffer solution sufficient to provide in the unknown reaction mixture renin and angiotensinogen concentrations at which there is no substantial angiotensin I generation at the temperatures to which the generated unknown radioimmunoassay reaction mixture is subsequently exposed. The reaction mixture is incubated at a temperature of at least about 12°C. so that a competitive binding reaction takes place between the antibody and both labeled and unlabeled angiotensin I. Bound angiotensin I is separated from unbound angiotensin I and the relative proportions of bound and unbound labeled angiotensin I in the reaction mixture are determined. The angiotensin I content of the generated unknown reaction mixture is determined by comparison of the relative proportions of bound and unbound labeled angiotensin I in the reaction mixture with the relative proportions of bound and unbound labeled angiotensin I in standard radioimmunoassay reaction mixtures containing known amounts of unlabeled angiotensin I. The renin activity of the plasma is determined from the difference between the angiotensin I content of the generated unknown reaction mixture and the angiotensin I content of an ungenerated radioimmunoassay reaction mixture containing a sample of the same unknown plasma. A kit useful in carrying out the method of the invention is also disclosed.

24 Claims, 4 Drawing Figures

3,966,896

RADIOIMMUNOASSAY FOR PLASMA RENIN ACTIVITY

BACKGROUND OF THE INVENTION

This invention relates to the field of in vitro radioimmunoassays and, more particularly, to an improved radioimmunological method for assaying plasma renin activity.

Hypertensive disease is often associated with high levels of aldosterone in the blood. In primary aldosteronism, this condition results from disease directly involving the adrenal gland. In renal vascular disease, on the other hand, high aldosterone levels may result from high concentrations of angiotensin II in in the blood. Angiotensin II is a potent vasopressor and stimulates production of aldosterone by the adrenal gland. Thus, in both primary aldosteronism and renal vascular disease, high levels of aldosterone may be observed in the blood and aldosterone level, as such, does not provide a basis for distinguishing between these two different causes of hypertension.

It is well recognized that primary aldosteronism can be distinguished from angiotensin II-induced aldosterone secretion by measurement of plasma renin activity. Renin is a proteolytic enzyme secreted by juxtaglomerular cells in the kidney. Angiotensinogen, an $\alpha$-2-globulin produced by the liver, is converted by renin to the decapeptide angiotensin I. Although itself biologically inactive, angiotensin I is converted to angiotensin II in the pulmonary circulation. In patients suffering from renal hypertension, the plasma renin activity, and thus the angiotensin generation rate, is high, while in primary aldosteronism renin activity is low.

Bioassay techniques are known for the determination of plasma renin activity. The convenience of making renin acitivity determinations has been greatly enhanced, however, by the development of radioimmunoassay techniques for its measurement. Radioimmunoassay is a method based on the phenomenon of competitive protein binding in which a reaction system is prepared containing a known amount of radioactively labeled antigen, an unknown amount of unlabeled antigen to be assayed, and a standard amount of an antibody for the antigen. The system is incubated at a predetermined temperature for a predetermined time sufficient for the competitive reaction of the labeled and unlabeled antigen with the antibody to proceed to an analytically significant extent. The proportion of labeled antigen bound to antibody in the assay reaction system is then determined by radioactive counting. This determination also establishes the proportion of unlabeled antigen bound to antibody and, by inference, the amount of unlabeled antigen initially charged to the reaction system.

Competitive protein binding assays are conventionally illustrated by the following reaction equations:

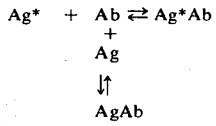

where
Ag* = radioactively labeled antigen
Ag = unlabeled antigen
Ab = antibody specific for Ag/Ag*
Ag*Ab = labeled antigen/antibody complex
AgAb = unlabeled antigen/antibody complex Provided that the total of labeled and unlabeled antigens is in excess, unlabeled antigen from an unknown sample competes with the labeled antigen for the binding sites on the antibody. For given quantities of antibody and labeled antigen, the proportion of labeled antigen bound to the antibody decreases with increasing amounts of unlabeled antigen in the reaction system. Using standard known quantities of unlabeled antigen, data may be developed correlating the ratio of bound to free labeled antigen with the amount of unlabeled antigen in the reaction system. A curve developed from such data may then be used to determine the quantities of the unlabeled antigen in a test reaction system to which a sample containing an unknown quantity of unlabeled antigen has been charged.

Since no radioimmunoassay methods are presently available for directly determining the quantity of renin in a plasma sample, renin activity is measured in terms of the rate of angiotensin I generation in the sample. Methods are available in which a plasma sample is divided, one portion kept in the cold to prevent significant angiotensin I generation and the other sample incubated at elevated temperature, for example, body temperature, to cause generation of angiotensin I by action of renin on angiotensinogen. Inhibitors are included in the generation mixture to prevent either formative of angiotensin II by action of converting enzymes on angiotensin I or destruction of angiotensin I by various proteolytic enzymes. After the generation step is complete, both the generated sample and the base sample which had been kept in the cold are subjected to radioimmunoassay for determination of angiotensin I content. The difference between the angiotensin I content of the generated sample and that of the base sample may be divided by the time of generation in order to determine renin activity in terms of angiotensin I generated per unit volume per unit time.

A serious drawback of previously available radioimmunoassay methods for measurement of renin activity is the necessity of carrying out the radioimmunoassay step in the cold, typically at 4°C. Because of the presence of renin in both the base sample and the generated sample, it has been thought necessary to use such low temperatures in order to avoid error introduced by generation or destruction of angiotensin I during the radioimmunoassay. As a consequence of the low temperatures which are used, the time required for adequate reaction is long, for example, 18–24 hours. Such lengthy incubation times are obviously inconvenient and render the assay more expensive.

An unfulfilled need has, therefore, existed for an improved radioimmunoassay method for determining plasma renin activity which does not require the extensive incubation period heretofore considered necessary to avoid incidental angiotensin I generation.

SUMMARY OF THE INVENTION

It is an object of the present invention, therefore, to provide an improved radioimmunoassay method for measurement of plasma renin activity. It is a particular object of the present invention to provide such a method in which the radioimmunoassay can be carried out within a substantially shorter period of time than has been conventionally considered feasible. It is a further object of the present invention to provide such a method in which a sharp, definitive separation is realized between bound and unbound labeled angiotensin I. Other objects and features will be in part apparent and in part pointed out hereinafter.

Briefly, therefore, the present invention is directed to a radioimmunoassay method for the in vitro determination of the renin activity of an unknown plasma sample. In this method an unknown generation sample is provided by mixing the unknown plasma sample with a generation buffer solution and an inhibitor for enzymes which convert angiotensin I to other substances. The unknown generation sample is incubated to generate angiotensin I therein by action of renin upon angiotensinogen, thereby producing a generated unknown sample. A generated unknown radioimmunoassay reaction mixture is provided by mixing the generated unknown plasma sample with a predetermined amount of radioactively labeled angiotensin I, a predetermined amount of an antibody for angiotensin I, and an amount of an assay buffer solution sufficient to provide in the generated unknown reaction mixture renin and angiotensinogen concentrations at which there is no substantial angiotensin I generation at the temperatures to which the generated unknown radioimmunoassay reaction mixture is subsequently exposed. The generated unknown radioimmunoassay reaction mixture is incubated at a temperature of at least about 12°C. so that a competitive binding reaction takes place between the antibody and both labeled and unlabeled angiotensin I. Bound angiotensin I is separated from unbound angiotensin I, and the relative proportions of bound and unbound labeled angiotensin I in the reaction mixture are determined. The angiotensin I content of the generated unknown reaction mixtures is determined by comparison of the relative proportions of bound and unbound labeled angiotensin I in the unknown reaction mixture with the relative proportions of bound and unbound labeled angiotensin I in standard radioimmunoassay reaction mixtures containing known amounts of unlabeled angiotensin I. The renin activity of the plasma is determined from the difference between the angiotensin I content of the generated unknown reaction mixture and the angiotensin I content of a nongenerated radioimmunoassay reaction mixture containing a sample of the same unknown plasma.

The invention is further directed to a packaged test kit for use in a radioimmunoassay method for the in vitro determination of the renin activity of blood plasma. The kit comprises the combination of a generation buffer solution comprising a buffering component selected from the group consisting of potassium acid phthalate and 2,2-dimethyl glutaric acid; a reaction medium having a pH of approximately 9 and comprising a buffering component, human serum albumin, an alkali metal azide, and radioactively labeled angiotensin I; an antiserum containing an antibody for angiotensin I; a plurality of standard solutions containing known amounts of unlabeled angiotensin I; and a plurality of relatively thin strips of a membrane consisting essentially of an ion exchange resin.

BRIEF DESCRIPTION OF THE DRAWINGS

Corresponding reference characters indicate corresponding parts throughout the several views of the drawings.

DESCRIPTION OF THE PREFERRED EMBODIMENTS

Figure 1:
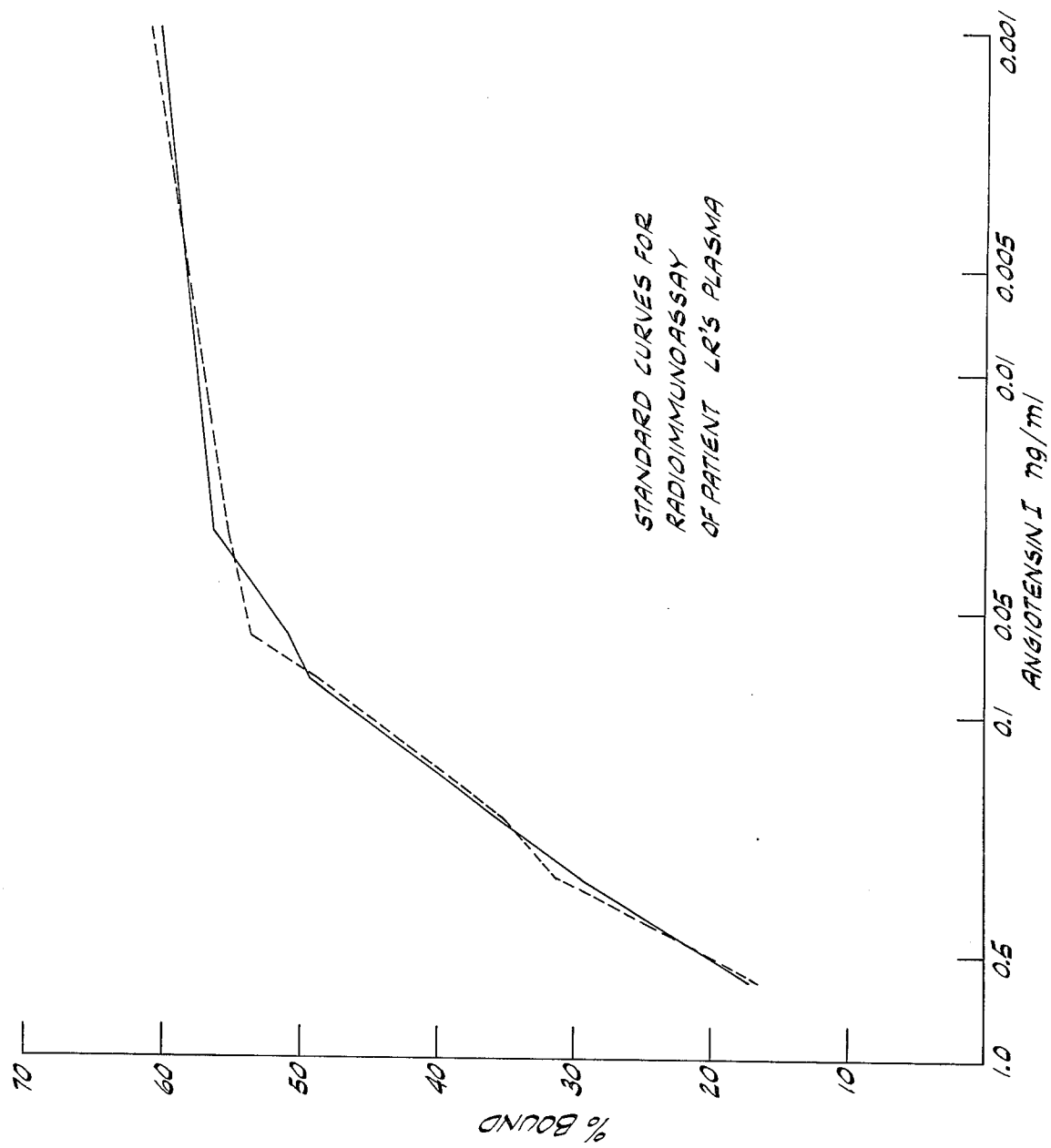
FIG. 1 is a standard semi-log graph used in the analysis of the plasma renin activity of patient LR indicating the percent labeled angiotensin I bound to the antibody as a function of the angiotensin I content of standard radioimmunoassay reaction systems.

In accordance with the present invention, it has now been discovered that, if the radioimmunoassay reaction system is sufficiently dilute, the radioimmunoassay of angiotensin I for determination of plasma renin activity can be carried out at temperatures substantially above 4°C. without incidental generation of further significant quantities of angiotensin I. Surprisingly, in view of the previous adherence to assay incubation temperatures of 4°C., it has been found that adequate dilution allows the assay to be very conveniently carried out at temperatures on the order of 37°C. to provide reproducible data which definitively identifies both high and low plasma renin activity. At such temperatures, adequate dilution practically eliminates angiotensin I generation yet allows the immunological equilibration reaction to proceed rapidly. By conducting the assay at the relatively elevated temperatures now found feasible, a major reduction is thus achieved in the time required to carry out the radioimmunoassay, and the cost of determining plasma renin activity is substantially reduced while the convenience of the test is greatly enhanced.

In a clinical procedure utilizing the process of the invention, the plasma is treated with an inhibitor for enzymes which convert angiotensin I to other substances, then mixed with a buffer to provide an unknown generation sample. The unknown generation sample is incubated to provide a generated unknown sample, while a base unknown sample of the same composition is diluted and kept at about 37°C. or below during incubation of the generation sample so that significant conversion of angiotensinogen to angiotensin I is avoided in the base sample. A radioimmunoassay is run on both the generated unknown and the base unknown samples in radioimmunoassay reaction mixtures of sufficient dilution so that generation of angiotensin I is avoided at the temperature at which the assay competitive binding reaction is conducted. Following the assay reaction, each assay reaction mixture is processed to separate bound from unbound angiotensin I and, by counting radioactivity, the relative proportions of bound and unbound labeled angiotensin I are measured. The angiotensin I contents of both the base unknown radioimmunoassay reaction mixture and the generated unknown reaction mixture are determined by reference to a standard curve derived from radioimmunoassays run on reaction mixtures containing varying known amounts of unlabeled angiotensin I and the same invariant proportions of labeled antigen and antibody as the unknown reaction systems. The standard curve is constructed by plotting a function of the relative proportions of bound and unbound labeled angiotensin I versus a function of the known amounts of unlabeled angiotensin I contained in the standard reaction mixtures.

To initiate the procedure, the patient's blood is drawn into a tube, cooled immediately to a temperature of 4°C. or less, and the plasma separated by centrifugation. If the plasma is to be held for any significant period of time, it should be frozen. It is strongly preferable, however, that the radioimmunoassay test be run the same day that the blood is drawn.

As in conventional practice, the tube into which the blood is drawn is coated with a chelating agent such as ethylenediamine tetraacetic acid. This chelating agent not only acts as an anticoagulant but inhibits the activity of proteolytic enzymes contained in the serum, thereby preventing destruction of angiotensin I or other proteins contained in the blood.

The cold plasma sample is conveniently divided into aliquots. One of these aliquots is used for generation while the second (base) aliquot is used to carry out the base radioimmunoassay. To the plasma sample, or each aliquot thereof, is added an inhibitor for enzymes which convert angiotensin 1 to other substances. In particular, it is necessary to include an inhibitor for the converting enzyme which converts angiotensin I to angotensin II, and also for the angiotensinases which break down angiotensin I and angiotensin II.

Useful inhibitors include 8-hydroxyquinoline and 2,3-dimercaptopropanol, both of which are preferably mixed with the plasma sample. Effective inhibition is provided, for example, by dosing the plasma with approximately 4.5 moles/l of 8-hydroxyquinoline and approximately 8 moles/l of 2,3-dimercaptopropanol.

As noted, it is highly perferable that the generation and radioimmunoassay incubations be carried out on the same day that the blood is drawn. However, if there is to be any significant delay between the drawing of the plasma and carrying out of the assay procedure, the plasma containing the inhibitor should be frozen and stored at a temperature of approximately −20°C.

On the date that the assay is to be carried out, an unknown generation sample is prepared by mixing the inhibited generation aliquot of plasma with a generation buffer solution. Preferably, one part by volume inhibited plasma is diluted with two parts by volume buffer. An aliquot of the generation sample may be further diluted and used as the base unknown sample. Generation is carried out by warming the generation sample and maintaining it at a temperature at which the renin activity is sufficiently high to cause conversion of angiotensinogen to angiotensin I at an appreciable rate. Since renin activity is optimized at a pH of approximately 5.5, the buffer utilized is preferably one which stabilizes the generation sample at or near that pH. Preferred buffers include potassium acid phthalate and 2,2,-dimethyl glutaric acid. The latter buffer is especially effective in promoting rapid generation and survival of angiotensin I. Preferably, the buffering solution is approximately 0.1 molar in the buffering component.

To provide a renin activity sufficient to generate angiotensin I at an appreciable rate, the temperature of the generation sample is maintained at between about 10°C., and about 60°C., preferably 35°C–50°C. during the generation process. The most preferred temperature for the generation incubation is approximately 37°C. Generation may be carried out in an hour or less but is preferably extended to a period of approximately 3 hours at 37°C. so that the subsequent radioimmunoassay is sensitive to abnormally low renin activity as well as high activity.

The second (base) aliquot of plasma is also diluted with assay buffer to provide a base unknown sample which may be assayed at any convenient time. As noted, the base unknown may be an aliquot of the generation unknown sample already diluted with buffer. Preferably, the base unknown sample is further diluted and held at 37°C. or below during generation of the unknown generation sample so that the generated and base radioimmunoassay are later carried out simultaneously. In any event, both generated and base unknown radioimmunoassay reaction mixtures are prepared containing the same proportions of the respective plasma unknowns, labeled angiotensin I, antiserum for angiotensin I and assay buffer solution. The concentrations of renin and angiotensinogen in each reaction system are sufficiently low so there is no substantial angiotensin I generation at the temperatures to which the reaction systems are subsequently exposed. So that the labeled and unlabeled angiotensin I contained in the reaction mixtures will compete for the binding sites on the antibody, the amount of antiserum contained in the reaction mixture is less that that required to bind all of the antigen contained therein. Preferably the antibody content of the reaction mixture is sufficient to bind about 50% of the labeled antigen in the absence of any unlabeled antigen.

The assay buffer solution contained in the reaction mixtures comprises a buffering component, excess protein and a preservative. To minimize the probability of significant angiotensin I generation during the radioimmunoassay reaction, the buffering component of the assay buffer solution is preferably one which maintains the pH of the reaction mixture at approximately 9. A suitable buffering component is tris (hydroxymethyl) aminomethane at a molarity on the order of 0.08.

The presence of excess protein (e.g., 0.5% by weight of the buffer solution) in the buffer solution functions to stabilize both the antigen and antibody and thus the immunological reaction. The presence of this protein also serves to inhibit nonspecific adsorption of reaction components on the container wall. Human serum albumin is preferably used as the excess protein since the antiserum utilized in the assay is derived from an animal and is thus unlikely to include antibodies for human serum albumin. Additionally, human serum albumin is, of course, compatible with the plasma sample obtained from a human.

A preservative suitable for inclusion in the assay buffer solution is an alkali metal azide. Sodium azide in a proportion of about 0.01% by weight of the buffer solution is preferred.

In a preferred embodiment of the invention, the assay buffer solution is precombined with the labeled angiotensin I to provide a reaction medium to which the generated unknown plasma sample and the antiserum containing the antibody are added at the outset of the assay reaction. The same reaction medium is preferably used to initially dilute the base aliquot and provide a base prereaction system. After generation is complete, antiserum is added to the prereaction mixture to provide the base radioimmunoassay reaction mixture that is reacted in parallel with the generated unknown reaction mixture.

It is essential that the volume of the reaction medium be sufficient to dilute the renin and angiotensinogen concentrations to levels at which there is no substantial angiotensin I generation in the radioimmunoassay reaction mixture at the temperatures to which the reaction mixture is exposed. Normally, the renin and angiotensinogen concentrations in the reaction mixture should not exceed about 1/10 of the concentrations of these two components in the plasma itself. Preferably a twenty-fold or greater dilution is used.

The radioimmunoassays are carried out by incubating the generated and base unknown reaction mixtures at the same temperature for the same period of time. In order for the competitive protein binding reaction to progress to a sufficient extent within a convenient time, for example, 15 minutes to 5 hours, preferably 15 minutes to 3 hours, the assay reaction should be carried out at a temperature of at least about 12°C. Preferably, the assay temperature should be at least about 20°C. If a temperature of 37°C. is used, as is highly preferred, an adequate assay reaction is complete in approximately 1 hour. Temperatures above 37°C. can be utilized but are generally unnecessary. There is essentially no practical advantage in running above 40°C. If excessive temperatures are employed, denaturing of protein begins to occur at excessive rates, and temperatures above about 55°C. should be avoided.

When the radioimmunoassay reactions are complete, bound and unbound angiotensin I are separated and the relative proportions of bound and unbound labeled angiotensin I are measured by counting radioactivity. The angiotensin I content of each reaction mixture is determined by reference to standard curves constructed from radioimmunoassays on known samples of unlabeled angiotensin I using reaction mixtures containing the same proportions of labeled angiotensin I and antiserum as the unknown reaction mixtures. The renin activity of the plasma is then determined from the difference between the angiotensin I concentration in the generated sample and that in the base sample.

Unbound angiotensin I may be separated from antibody-bound angiotensin I by any of the various methods which are well known in the art. Thus, for example, separation may be accomplished by electrophoresis, chromatoelectrophoresis, precipitation of the antibody/antigen complex by a second antibody, nonspecific salt precipitation, or adsorption on a solid adsorbing agent such as charcoal coated with dextran.

In a preferred embodiment of the invention, the unbound angiotensin I is separated from the bound angiotensin I by adsorption of the former on a relatively thin strip of a membrane consisting essentially of an ion exchange resin. The ion-exchange resin membranes which may be employed in the present invention are relatively thin strips, sheets or films of a solid hydrous gel consisting of an insoluble polymeric matrix to which are attached dissociable cationic or anionic groups, the gel being preferably reinforced with some suitable fibrous material. Many useful resin membranes of this kind are known, as for example those described in U.S. Pat. Nos. 2,730,768, 2,780,604, 2,800,445 and 2,860,097. For example, a commercially available anion-selective resin useful in the present invention is that marketed under the trade designation "AR-103-PZL-183" (by Ionics, Inc. of Watertown, Massachusetts). The use of such a resin strip provides highly effective separation of the unbound from the bound antigen since it is not only an effective scavenger for unbound antigen but is readily and easily separated from the reaction mixture after adsorption is complete. To carry out the separation, the resin strip is inserted in the reaction mixture after completion of the binding reaction and the reaction mixture is incubated in contact with the strip at room temperature or below, preferably 22°–25°C. for approximately ½ hour. After completion of incubation, the strip is removed and residual moisture wiped off on the lid of the reaction vial so that essentially all antibody-bound antigen is returned to the reaction mixture.

To determine the relative proportions of bound and unbound angiotensin I, the reaction mixture is counted for radioactivity both before insertion of the resin strip and after removal thereof. The percent labeled angiotensin I bound to the antibody is then equal to the postcount divided by the precount.

The packaged test kit of the invention allows the clinical technician to make rapid, accurate determinations of plasma renin activity. The kit includes vials variously containing generation buffer solutions, precombined reaction media, antisera, standard solutions of known amounts of unlabeled angiotensin I, and ion exchange resin membrane strips. Each reaction medium vial contains the proper volume of reaction medium and amount of labeled angiotensin I for carrying out one radioimmunoassay reaction. The labeled angiotensin I preferably contains $^{125}I$ but other labels such as $^{131}I$ may also be used.

The antiserum contained in the kit is preferably obtained by conjugating angiotensin I to bovine serum albumin and injecting the resulting immunogen into a rabbit. The serum subsequently withdrawn from the rabbit may be used directly or an antiserum may be provided by separating the γ-globulin antibody from the rabbit serum and preparing a solution of the antibody.

The following examples illustrate the invention:

EXAMPLE 1

A plasma renin activity radioimmunoassay kit was prepared containing 100 reaction vials, 4 antibody vials, 35 generation vials, 1 8-hydroxyquinoline inhibitor vial, 1 dimercaprol inhibitor vial, 2 vials each containing 100 anion exchange strips, and 9 vials each containing a standard angiotensin I solution.

The precombined reaction medium contained in each reaction vial had the following composition.

| | |
|---|---|
| Angiotensin I I-125 | .0202±.008 μCi |
| Human Serum Albumin | 5.0 mg |
| Trishydroxymethyl-aminomethane | 10.0 mg |
| Sodium azide | 0.1 mg |
| Hydrochloric acid | 23.83±2.97 μg |
| Water | 1 ml |

Each standard vial contained a known amount of unlabeled angiotensin I. The respective compositions of the solutions contained in these vials were:

| | |
|---|---|
| A. 10 ng/ml Standard | |
|   Glacial acetic acid | 60 ng |
|   Lysozyme | 60 μg |
|   Trishydroxymethyl-aminomethane | 10.1 mg |
|   Human Serum Albumin | 5 mg |
|   Sodium azide | 0.1 mg |
|   Hydrochloric Acid | 23.83±2.97 μg |
|   Angiotensin I | 10 ng |
|   Water | 1 ml |
| B. 6 ng/ml Standard | |
|   Glacial acetic acid | 35.8 ng |
|   Lysozyme | 35.8 μg |
|   Trishydroxymethyl-aminomethane | 10.1 μg |
|   Human Serum Albumin | 5 mg |
|   Sodium Azide | 0.1 mg |
|   Hydrochloric Acid | 23.83±2.97 μg |

-continued

| | |
|---|---|
| Angiotensin I | 6 ng |
| Water | 1 ml |
| C. 3 ng/ml Standard | |
| Glacial acetic acid | 17.95 ng |
| Lysozyme | 17.95 μg |
| Trishydroxymethyl-aminomethane | 10.1 mg |
| Human Serum Albumin | 5 mg |
| Sodium Azide | 0.1 mg |
| Hydrochloric Acid | 23.83±2.97 μg |
| Angiotensin I | 3 ng |
| Water | 1 ml |
| D. 2 ng/ml Standard | |
| Glacial Acetic Acid | 12 ng |
| Lysozyme | 12 μg |
| Trishydroxymethyl-aminomethane | 10.1 mg |
| Human Serum Albumin | 5 mg |
| Sodium Azide | 0.1 mg |
| Hydrochloric Acid | 23.83±2.97 μg |
| Angiotensin I | 2 ng |
| Water | 1 ml |
| E. 1 ng/ml Standard | |
| Glacial acetic acid | 6 ng |
| Lysozyme | 6 μg |
| Trishydroxymethyl-aminomethane | 10.1 mg |
| Sodium Azide | 0.1 mg |
| Human Serum Albumin | 5 mg |
| Hydrochloric Acid | 23.83±2.97 μg |
| Angiotensin I | 1 ng |
| Water | 1 ml |
| F. 0.8 ng/ml Standard | |
| Glacial Acetic Acid | 6 ng |
| Lysozyme | 6 μg |
| Trishydroxymethyl-aminomethane | 10.1 mg |
| Sodium Azide | 0.1 mg |
| Human Serum Albumin | 5 mg |
| Hydrochloric Acid | 23.83±2.97 μg |
| Angiotensin I | 1 ng |
| Water | 1 ml |
| G. 0.6 ng/ml Standard | |
| Glacial Acetic Acid | 3.59 ng |
| Lysozyme | 3.59 μg |
| Trishydroxymethyl-aminomethane | 10.1 mg |
| Sodium Azide | 0.1 mg |
| Human Serum Albumin | 5 mg |
| Hydrochloric Acid | 23.83±2.97 μg |
| Angiotensin I | 0.6 ng |
| Water | 1 ml |
| H. 0.3 ng/ml Standard | |
| Glacial Acetic Acid | 1.795 ng |
| Lysozyme | 1.795 μg |
| Trishydroxymethyl-aminomethane | 10.1 mg |
| Human Serum Albumin | 5 mg |
| Sodium Azide | 0.1 mg |
| Hydrochloric Acid | 23.8±2.97 μg |
| Angiotensin I | 0.3 ng |
| Water | 1 ml |
| I. 0 ng/ml Standard | |
| Trishydroxymethyl-aminomethane | 10.1 mg |
| Human Serum Albumin | 5 mg |
| Sodium Azide | 0.1 mg |
| Hydrochloric Acid | 23.83±2.97 μg |
| Water | 1 ml |

The antiserum solution contained in the antibody vials had the following composition:

| | |
|---|---|
| Antiserum (Rabbit) | 1.4 μl |
| Trishydroxymethyl-aminomethane | 28.28 mg |
| Human Serum Albumin | 14.0 mg |
| Sodium Azide | 0.28 mg |
| Hydrochloric Acid | 6.67±.83 μg |
| Water | 2.8 ml |

The generation buffer contained in the generation vials had the composition:

| | |
|---|---|
| Potassium Hydrogen Phthalate | 40.84 mg |
| Sodium Hydroxide | 216±65 μg |
| Water | 2 ml |

The 8-hydroxyquinoline inhibiting solution had the composition:

| | |
|---|---|
| 8-hydroxyquinoline | 66 mg |
| Water | 1 ml |

The dimercaprol inhibiting solution had the composition:

| | |
|---|---|
| 2,3 dimercaptopropanol | 100 mg |
| Benzyl Benzoate | 210 mg |
| Peanut Oil | 680 mg |

Each of the 100 resin strips contained in the kit comprised an anhydrous anion exchange resin gel of the type sold under the trade designation "AR-103-PZL-183" (by Ionics, Inc. of Watertown, Massachusetts) reinforced with a fibrous material.

EXAMPLE 2

Using a kit of the type described in Example 1, a radioimmunoassay was carried out to determine the plasma renin activity of patient LR.

Blood was drawn from patient LR into a tube coated with EDTA and the plasma separated by centrifugation and cooled to 4°C. To one ml. of the cold plasma were added portions of 8-hydroxyquinoline inhibiting solution (10 μl) and dimercaprol inhibiting solution (10 μl). The resulting unknown plasma sample was transferred to a generation vial containing generation buffer solution and mixed.

A base unknown sample (100 μl) was withdrawn from the generation vial and immediately added to a reaction vial to provide a base unknown prereaction mixture containing ungenerated plasma, human serum albumin, sodium azide preservative, HCl and $^{125}$I labeled angiotensin I buffered to a pH of 9.0. This preparation mixture was held at room temperature during the subsequent generation of the portion of the unknown sample remaining in the generation vial.

The generation vial was placed in a water bath controlled at 37°C. and generation was carried out for 3 hours. At the end of this time, the generated unknown sample was removed from the water bath, cooled in an ice bath, and three 100 μl aliquots thereof transferred to three reaction vials to provide three generated unknown radioimmunoassay prereaction mixtures containing generated plasma, human serum albumin, sodium azide preservative, HCl, and $^{125}$I labeled angiotensin I.

A series of standard prereaction mixtures was prepared by transferring 0.1 ml aliquots of standard unlabeled angiotensin I solutions from the standard vials to a series of reaction vials. Standard prereaction mixtures were prepared using the standard solutions containing 6, 3, 2, 1, 0.8, 0.6, and 0.3 ng/ml unlabeled angiotensin I, respectively. Two blank prereaction mixtures were prepared by adding 0.1 ml pH 9.0 buffer to a reaction vial.

Reaction mixtures were prepared and radioimmunoassay commenced by adding antiserum solution (0.1 ml) to each of the base unknown, generated unknown, standard, and blank prereaction mixtures. Antiserum was withheld from one reaction vial used as a control.

The reaction mixtures contained in each vial were then mixed gently on a vortex and incubated for 1 hour at 37°C. After incubation was completed, each reaction vial was taken out of the water bath, the cap removed and an anion exchange resin strip immersed in the contents of the vial. The vial was then recapped and placed on a rotator for 30 minutes at room temperature (21°–23°C.). At the end of 30 minutes, the resin strip was removed from each vial and placed in an empty vial. Radioactivity of both the strip containing the unbound ("free") angiotensin I and the supernatant liquid containing the antibody bound ("bound") angiotensin I was counted, and the percentage bound angiotensin I was determined from the following relationship:

$$\% \text{ Bound} = \frac{\text{Count of supernatant liquid}}{\text{Count of supernatant} + \text{count of strip}}$$

The results of counting and the calculated percent bound angiotensin I for the standard reaction mixtures are set forth in Table I.

TABLE I

| Standard Reaction Systems Radioactivity Counts Per Minute | | | |
|---|---|---|---|
| Supernatant Liquid | | Strip | %Bound |
| Control (no antibody) | | 576 | 12409 | 4.44 |
| 0.6 | ng | 2253 | 10835 | 17.21 |
| 0.3 | ng | 3879 | 9284 | 29.47 |
| 0.2 | ng | 4700 | 8448 | 35.75 |
| 0.1 | ng | 5980 | 7041 | 45.93 |
| 0.08 | ng | 6404 | 6663 | 49.01 |
| 0.06 | ng | 6563 | 6365 | 50.77 |
| 0.03 | ng | 7231 | 5605 | 56.33 |
| 0.0 | ng | 7665 | 5165 | 59.74 |
| 0.0 | ng | 7706 | 5061 | 60.36 |

A duplicate set of standard radioimmunoassay reactions provided the data set forth in Table II.

TABLE II

| Duplicate Standard Reaction Systems Radioactivity Counts Per Minute | | | |
|---|---|---|---|
| Supernatant Liquid | | Strip | %Bound |
| 0.6 | ng | 2150 | 10877 | 16.50 |
| 0.3 | ng | 3972 | 8709 | 31.32 |
| 0.2 | ng | 4473 | 8289 | 35.05 |
| 0.1 | ng | 5814 | 7053 | 45.19 |
| 0.08 | ng | 6190 | 6540 | 48.63 |
| 0.06 | ng | 6826 | 5902 | 53.62 |
| 0.03 | ng | 7016 | 5693 | 55.20 |
| 0.0 | ng | 7812 | 5046 | 60.76 |
| 0.0 | ng | 8060 | 5068 | 61.40 |

From the data of Tables I and II, a graph was prepared in which the percent bound angiotensin I was plotted against nanograms of unlabeled standard angiotensin I contained in the standard reaction solutions for the two sets of standard reactions. FIG. 1 is that graph.

The radioactivity counting data for patient LR's plasma is set forth in Table III. From the percentage bound $^{125}$I labeled angiotensin I, the proportion of unlabeled angiotensin I in each unknown plasma sample was determined from the curves of FIG. 1. This data is also set forth in Table III.

TABLE III

| Radioactivity Counting for LR Plasma (Phthalate Generation Buffer) | | | |
|---|---|---|---|
| | Supernatant Liquid | Strip | %Bound | Angiotensin I (ng/ml) |
| base generated (in triplicate) | 7463 | 5607 | 57.10 | 0.014 |
| | 6510 | 6677 | 49.36 | |
| | 6729 | 6018 | 52.79 | |
| | 6605 | 6314 | 51.13 | |
| generated (avg.) | | | 51.09 | 0.056 |

The renin activity of patient LR's plasma was indicated by the angiotensin I generation rate determined from the following relationship:

Renin activity (ng/ml/hr. angiotensin I generation) =
$$\frac{[\text{ng/ml (generated)} - \text{ng/ml (base)}]30}{3 \text{ hrs.}}$$

The factor of 30 is used because the plasma is initially diluted three-fold, and only 0.1 ml of the dilute plasma is used in the radioimmunoassay, while the angiotensin I generation rate is based on 1 ml.

Renin activity of LR plasma was determined to be 0.42 ng/ml/hr.

EXAMPLE 3

Another sample of patient LR's plasma was assayed in the manner described in Example 2, except that 2,2-dimethyl glutaric acid was used in place of potassium acid phthalate as the buffering component of the generation mixture. Results of radioactivity counting on the base and generated radioimmunoassay reaction mixtures obtained in the assay of this example are set forth in Table IV.

TABLE IV

| Radioactivity Counting for LR Plasma (Glutarate Generation Buffer) | | | |
|---|---|---|---|
| | Supernatant Liquid | Strip | %Bound | Angiotensin I (ng/ml) |
| base generated (in triplicate | 8025 | 4979 | 61.71 | 0 |
| | 6404 | 6565 | 49.34 | |
| | 6632 | 6459 | 50.66 | |
| | 6485 | 6541 | 49.79 | |
| generated (avg.) | | | 49.93 | 0.07 |

In this assay, the renin activity was determined to be 0.7 ng angiotensin I/ml/hr.

EXAMPLE 4

Following the procedure described in Example 2, a renin activity radioimmunoassay was conducted on the plasma of patient GM. The results of radioactive counting and the percent bound antigen for the duplicate standard radioimmunoassay reaction mixture are set forth in Tables V and VI.

TABLE V

| Standard Reaction Systems Radioactivity Counts Per Minute | | | |
|---|---|---|---|
| Supernatant Liquid | | Strip | %Bound |
| Control (no antibody) | | 772 | 12627 | 5.76 |
| 0.6 | ng | 2369 | 10804 | 17.98 |
| 0.3 | ng | 3717 | 9530 | 28.06 |

TABLE V-continued

| | | Standard Reaction Systems Radioactivity Counts Per Minute | | |
|---|---|---|---|---|
| Supernatant Liquid | | | Strip | %Bound |
| 0.2 | ng | 3986 | 9524 | 29.50 |
| 0.1 | ng | 6046 | 7328 | 45.21 |
| 0.08 | ng | 6462 | 6956 | 48.16 |
| 0.06 | ng | 6618 | 6805 | 49.30 |
| 0.03 | ng | 7477 | 6353 | 54.06 |
| 0.0 | ng | 8094 | 5458 | 59.73 |
| 0.0 | ng | 8122 | 5563 | 59.35 |

TABLE VI

| | | Duplicate Standard Reaction Systems Radioactivity Counts Per Minute | | |
|---|---|---|---|---|
| Supernatant Liquid | | | Strip | %Bound |
| 0.6 | ng | 2306 | 10944 | 17.40 |
| 0.3 | ng | 3580 | 10032 | 26.30 |
| 0.2 | ng | 3801 | 9589 | 28.39 |
| 0.1 | ng | 5780 | 7625 | 43.12 |
| 0.08 | ng | 6330 | 6783 | 48.27 |
| 0.06 | ng | 6540 | 6764 | 49.16 |
| 0.03 | ng | 7325 | 6173 | 54.27 |
| 0.0 | ng | 8386 | 5526 | 60.28 |
| 0.0 | ng | 8165 | 5615 | 59.25 |

Figure 2:
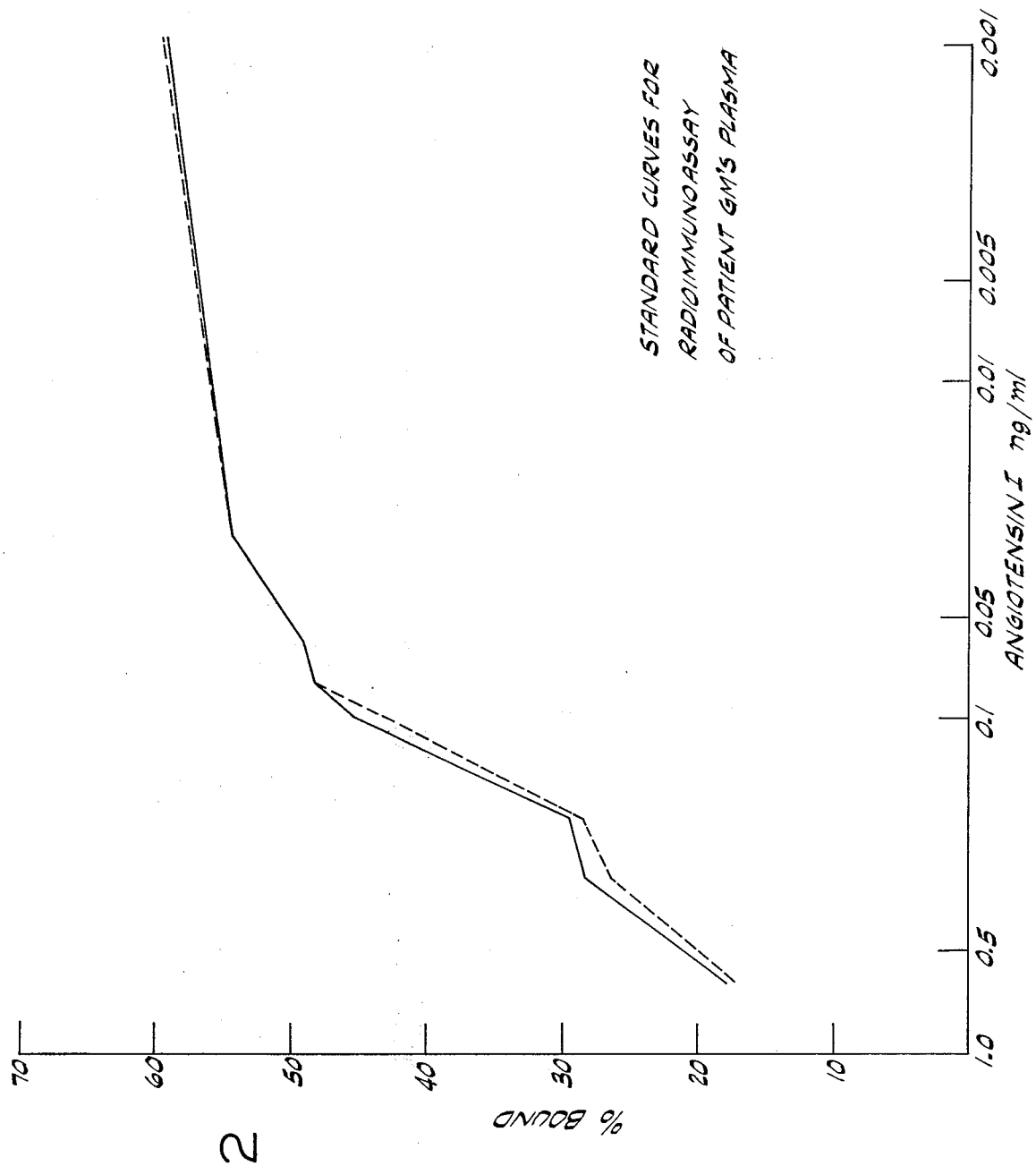
FIG. 2 is a plot similar to FIG. 1 showing the standard curve used in the analysis of the plasma renin activity of patient GM.

The data of Tables V and VI was plotted to provide FIG. 2 which was used for the determination of angiotensin I content of the plasma contained in the base and generated unknown radioimmunoassay reaction mixtures for patient GM.

The radioactivity counting results, percent bound antigen, and angiotensin I content of plasma for the base and generated unknown radioimmunoassay reaction mixtures containing patient GM's plasma are set forth in Table VII.

TABLE VII

| | Radioactivity Counting for GM Plasma (Phthalate Generation Buffer) | | | |
|---|---|---|---|---|
| | Supernatant Liquid | Strip | %Bound | Angiotensin I (ng/ml) |
| base | 7738 | 6071 | 56.04 | 0.009 |
| generated (duplicate) | 4935 | 8750 | 36.06 | |
| | 4727 | 8742 | 35.09 | |
| generated (avg.) | | | 35.58 | 0.153 |

The renin activity of GM plasma was determined to be 1.41 ng Angiotensin I/ml/hr.

EXAMPLE 5

Another sample of patient GM's plasma was assayed in the manner described in Example 4, except that 2,2-dimethylglutaric acid was used in place of potassium acid phthalate as a buffering component of the generation mixture. Results of radioactive counting on the base and generated radioimmunoassay mixtures obtained in the assay of this example are set forth in Table VIII.

TABLE VIII

| | Radioactivity Counting for GM Plasma (Glutarate Generation Buffer) | | | |
|---|---|---|---|---|
| | Supernatant Liquid | Strip | %Bound | Angiotensin I (ng/ml) |
| base | (Ungenerated phthalate values used- see Table VII) | | | |
| generated (duplicate) | 3.977 | 10122 | 28.21 | |
| | 3.943 | 10088 | 28.10 | |
| generated (avg.) | | | 28.15 | 0.3 |

In the assay of this example, the renin activity of GM plasma was determined to be 2.91 ng/ml/hr.

EXAMPLE 6

A renin activity radioimmunoassay was conducted on the plasma of patient PS. The procedure described in Example 2 was followed except that only one set of reactions was carried out in establishing the standard curve. Results of radioactive counting and the percent bound antigen for the standard radioimmunoassay reaction mixtures are set forth in Table IX.

TABLE IX

| | | Standard Reaction Systems Radioactivity Counts Per Minute | | |
|---|---|---|---|---|
| Supernatant Liquid | | | Strip | %Bound |
| Control | | 695 | 12013 | 5.47 |
| 0.6 | ng | 2224 | 10404 | 17.61 |
| 0.3 | ng | 3456 | 9088 | 27.55 |
| 0.2 | ng | 4486 | 8342 | 34.97 |
| 0.1 | ng | 5912 | 6743 | 46.72 |
| 0.08 | ng | 6373 | 6653 | 48.93 |
| 0.06 | ng | 6628 | 5935 | 52.76 |
| 0.03 | ng | 7191 | 5481 | 56.75 |
| 0.0 | ng | 7911 | 5089 | 60.84 |

Figure 3:
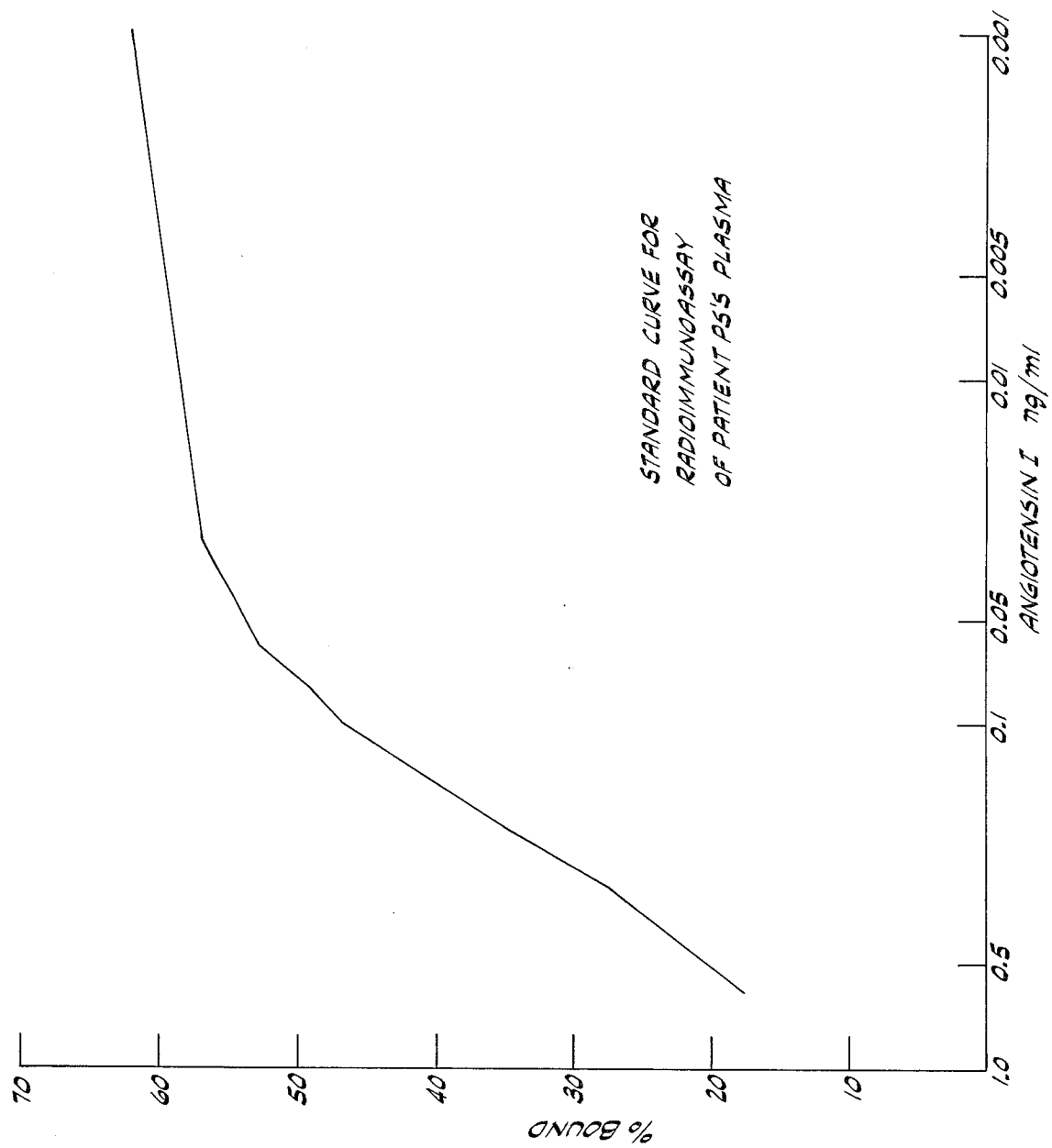
FIG. 3 is a graph similar to FIG. 1 used in the determination of the plasma renin activity of patient PS.

The data of Table IX was plotted to provide FIG. 3 which was used for the determination of angiotensin I content of the plasma contained in the base and generated unknown radioimmunoassay reaction mixtures for patient PS.

The radioactivity counting results, percent bound antigen, and angiotensin I content of plasma for the base and generated unknown radioimmunoassay reaction mixtures containing PSI plasma are set forth in Table X.

TABLE X

| | Radioactivity Counting for PS Plasma (Phthalate Generation Buffer) | | | |
|---|---|---|---|---|
| | Supernatant Liquid | Strip | %Bound | Angiotensin I (ng/ml) |
| base | 7190 | 5510 | 56.61 | 0.0315 |
| generated (triplicate) | 5828 | 7217 | 44.68 | |
| | 5909 | 7433 | 44.29 | |
| | 5908 | 6999 | 45.27 | |
| generated (avg.) | | | 44.75 | 0.114 |

The renin activity of PS's plasma was determined to be 0.849 ng/ml/hr.

EXAMPLE 7

Another sample of patient PS's plasma was assayed in the manner described in Example 6, except that 2,2-dimethylglutaric acid was used in place of potassium acid phthalate as the buffering component of the generation mixture. Results of radioactivity counting on the base and generated radioimmunoassay reaction mixtures, together with the angiotensin I content of the ungenerated and generated samples, are set forth in Table XI.

TABLE XI

Radioactivity Counting for PS Plasma (Glutarate Generation Buffer)

| | Supernatant Liquid | Strip | %Bound | Angiotensin I (ng/ml) |
|---|---|---|---|---|
| base | 7979 | 4840 | 62.24 | 0 |
| generated (triplicate) | 5433 | 7289 | 4271 | |
| | 5416 | 7539 | 4181 | |
| | 5248 | 7316 | 4177 | |
| generated (avg.) | | | 42.1 | 0.131 |

In this assay, the renin activity was determined to be 1.31 ng/ml/hr.

EXAMPLE 8

Standard radioimmunoassay reactions were carried out using duplicate blanks and standard solutions respectively containing 0.03, 0.06, 0.08, 0.1, 0.2, 0.3 and 0.6 ng. unlabeled angiotensin I per ml. A control was also run in which no antiserum was added to the prereaction mixture. The procedure of Example 2 was followed, except that the temperature and period of incubation of the radioimmunoassay reaction were varied. The following combinations of time and temperature were utilized for these standard radioimmunoassay reactions:

| Temperature | Time |
|---|---|
| 37°C. | 1 hr. |
| 20°C. | 1 hr. |
| 20°C. | 5 hr. |
| 12°C. | 1 hr. |
| 12°C. | 5 hr. |

The results of counting the supernatent liquid and resin strips after separation thereof, and the calculated percent bound angiotensin I for these standard reaction mixtures, are set forth in Tables XII through XVI.

TABLE XII

Standard Reaction System 37°C. for One Hour
Radioactivity Counts Per Minute

| | Supernatant Liquid | Strip | %Bound |
|---|---|---|---|
| Control (no antibody) | 592 | 11207 | 5.02 |
| 0.6 ng std. | 1982 | 9869 | 16.72 |
| 0.3 ng std. | 3304 | 8700 | 27.52 |
| 0.2 ng std. | 3620 | 8137 | 30.79 |
| 0.1 ng std. | 5019 | 6664 | 42.96 |
| 0.08 ng std. | 5089 | 6062 | 45.64 |
| 0.06 ng std. | 5769 | 5801 | 49.86 |
| 0.03 ng std. | 6310 | 5302 | 54.34 |
| 0.0 ng std. | 4848 | 3951 | 55.10 |
| 0.0 ng std. | 6384 | 4041 | 61.24 |

TABLE XIII

Standard Reaction System 20°C. for One Hour
Radioactivity Counts Per Minute

| Supernatant Liquid | Strip | %Bound |
|---|---|---|
| 0.6 | 1772 | 9629 | 15.54 |
| 0.3 | 2659 | 8554 | 23.71 |
| 0.2 | 3572 | 7373 | 31.21 |
| 0.1 | 4587 | 6815 | 40.23 |
| 0.08 | 3986 | 6530 | 37.90 |
| 0.06 | 5052 | 6462 | 43.88 |
| 0.03 | 5473 | 6293 | 46.52 |
| 0.0 | 5744 | 5968 | 49.04 |
| 0.0 | 5384 | 5767 | 48.28 |

TABLE XIV

Standard Reactions System 20°C. for Five Hours
Radioactivity Counts Per Minute

| Supernatant Liquid | Strip | %Bound |
|---|---|---|
| 0.6 | 1742 | 9872 | 15.0 |
| 0.3 | 2863 | 8475 | 25.25 |
| 0.2 | 3787 | 7963 | 32.23 |
| 0.1 | 5634 | 5573 | 50.27 |
| 0.08 | 6115 | 5265 | 53.73 |
| 0.06 | 7076 | 4323 | 62.08 |
| 0.03 | 7486 | 4171 | 64.22 |
| 0.0 | 7816 | 3586 | 68.55 |
| 0.0 | 7599 | 4361 | 63.54 |

TABLE XV

Standard Reactions System 12°C. for One Hour
Radioactivity Counts Per Minute

| Supernatant Liquid | Strip | %Bound |
|---|---|---|
| 0.6 | 1823 | 9623 | 15.9 |
| 0.3 | 2922 | 8412 | 25.8 |
| 0.2 | 3115 | 8317 | 27.2 |
| 0.1 | 3897 | 7457 | 34.3 |
| 0.08 | 3980 | 7479 | 34.7 |
| 0.06 | 4221 | 7315 | 36.6 |
| 0.03 | 4406 | 7083 | 38.3 |
| 0.0 | 4764 | 6664 | 41.7 |
| 0.0 | 4742 | 6523 | 42.1 |

TABLE XVI

Standard Reactions System 12°C. for Five Hours
Radioactivity Counts Per Minute

| Supernatant Liquid | Strip | %Bound |
|---|---|---|
| 0.6 | 1816 | 9131 | 16.6 |
| 0.3 | 2791 | 8630 | 24.4 |
| 0.2 | 3859 | 7471 | 34.1 |
| 0.1 | 5366 | 5927 | 47.5 |
| 0.08 | 5747 | 5658 | 50.4 |
| 0.06 | 5974 | 5316 | 52.9 |
| 0.03 | 6889 | 4445 | 60.8 |
| 0.0 | 7046 | 4096 | 63.2 |
| 0.0 | 7748 | 3871 | 66.7 |

Figure 4:
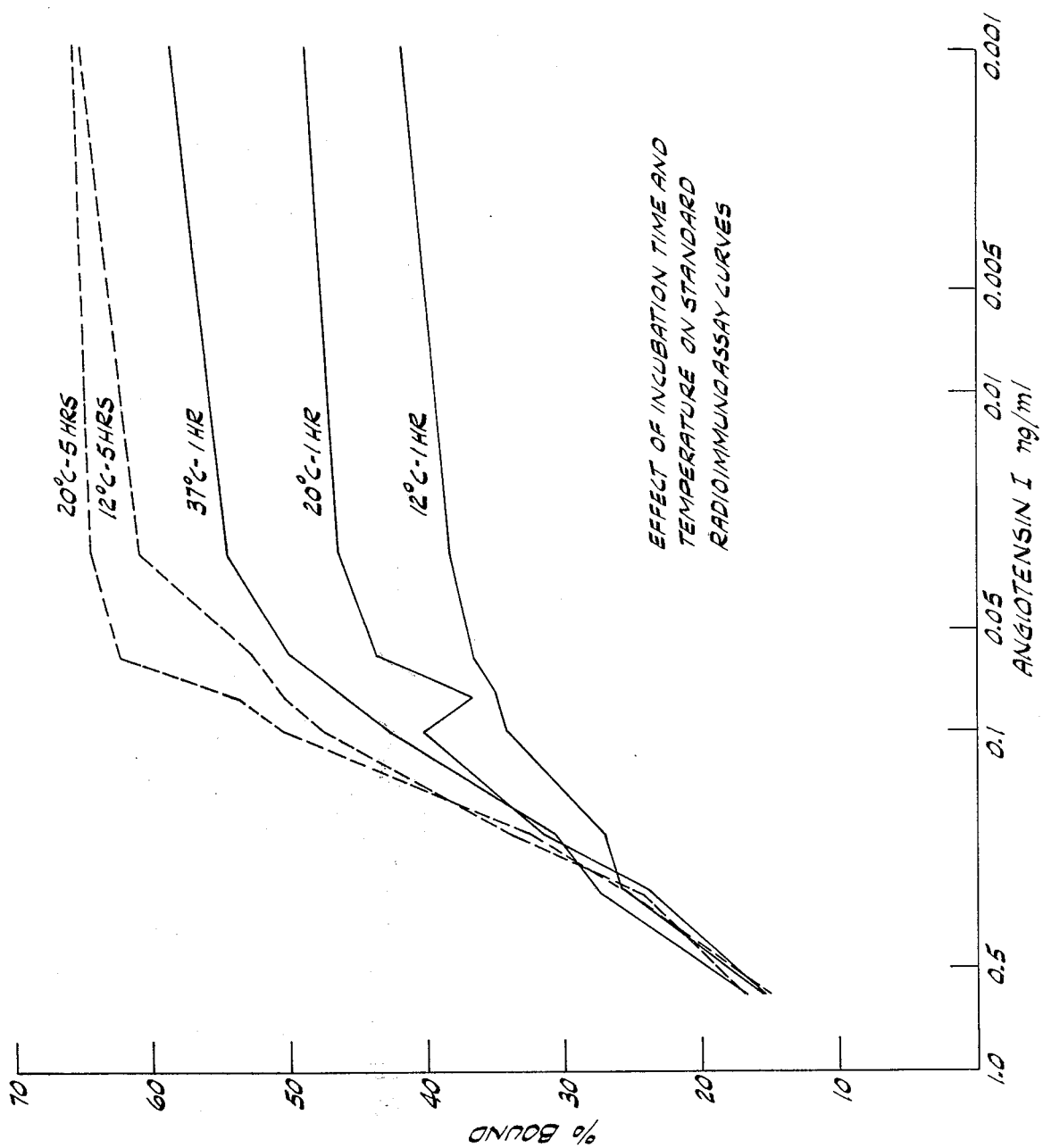
FIG. 4 is a graph which includes a series of curves similar to FIG. 1 but taken at different combinations of temperature and equilibration incubation times.

The data from each of Tables XII through XVI were plotted to provide a curve and this series of curves is set forth in FIG. 4.

The results of the standard reaction runs of this example demonstrate the feasibility of operating the radioimmunoassay reaction of the invention at a variety of temperatures within conveniently short periods of time.

In view of the above, it will be seen that the several objects of the invention are achieved and other advantageous results attained.

As various changes could be made in the above methods and products without departing from the scope of the invention, it is intended that all matter contained in the above description or shown in the accompanying drawings shall be interpreted as illustrative and not in a limiting sense.

What is claimed is:

1. A radioimmunoassay method for the in vitro determination of the renin activity of an unknown plasma sample, comprising the steps of:
  providing an unknown generation sample by mixing the unknown plasma sample with a generation buffer solution and an inhibitor for enzymes which convert angiotensin I to other substances;
  incubating said unknown generation sample to generate angiotensin I therein by action of renin upon angiotensinogen, thereby producing a generated unknown plasma sample;
  providing a generated unknown radioimmunoassay reaction mixture by mixing said generated unknown plasma sample with a predetermined amount of radioactively labeled angiotensin I, a predetermined amount of an antibody for angiotensin I, and an amount of an assay buffer solution sufficient to provide in said generated unknown reaction mixture renin and angiotensinogen concentrations at which there is no substantial angiotensin I generation at the temperatures to which said generated unknown radioimmunoassay reaction mixture is subsequently exposed;
  incubating said generated unknown radioimmunoassay reaction mixture at a temperature of at least about 12°C. so that a competitive binding reaction takes place between the antibody and both labeled and unlabeled angiotensin I;
  separating bound angiotensin I from unbound angiotensin I;
  determining the relative proportions of bound and unbound labeled angiotensin I in said reaction mixture;
  determining the angiotensin I content of said generated unknown reaction mixture by comparison of the relative proportions of bound and unbound labeled angiotensin I in said unknown reaction mixture with the relative proportions of bound and unbound labeled angiotensin I in standard radioimmunoassay reaction mixture containing known amounts of unlabeled angiotensin I; and
  determining the renin activity of said unknown plasma sample from the difference between the angiotensin I content of said generated unknown reaction mixture and the angiotensin I content of a nongenerated radioimmunoassay reaction mixture containing a sample of the same unknown plasma.

2. A method as set forth in claim 1 wherein said generated unknown radioimmunoassay reaction mixture is incubated at a temperature of between about 12°C. and about 55°C.

3. A method as set forth in claim 2 wherein said generated unknown radioimmunoassay reaction mixture is incubated at a temperature of between about 20°C. and about 40°C.

4. A method as set forth in claim 3 wherein said generated unknown radioimmunoassay reaction mixture is incubated for a period of between about 15 minutes and about 3 hours.

5. A method as set forth in claim 4 wherein said generated unknown radioimmunoassay reaction mixture is incubated at a temperature of approximately 37°C.

6. A method as set forth in claim 5 wherein said generated unknown radioimmunoassay reaction mixture is incubated for a period of approximately 1 hour.

7. A method as set forth in claim 1 wherein the concentration of renin in said generated unknown radioimmunoassay reaction mixture is no greater than about 1/10 of the concentration of renin in said unknown plasma sample.

8. A method as set forth in claim 7 wherein the renin concentration in said generated unknown radioimmunoassay reaction mixture is no greater than about 1/20 of the concentration of renin in said unknown plasma sample.

9. A method as set forth in claim 1 wherein the pH of said generated unknown radioimmunoassay reaction mixture is on the order of about 9.

10. A method as set forth in claim 9 wherein said assay buffer solution comprises a buffering component, human serum albumin and an alkali metal azide.

11. A method as set forth in claim 1 wherein said generated unknown radioimmunoassay reaction mixture is prepared by adding said generated unknown sample and said antibody to a precombined reaction medium comprising said assay buffer solution and said radioactively labeled angiotensin I.

12. A method as set forth in claim 1 wherein the radioactively labeled angiotensin I contains $^{125}I$.

13. A method as set forth in claim 1 wherein said unbound angiotensin I is separated from bound angiotensin I by:
  immersing a relatively thin strip of a membrane consisting essentially of an ion exchange resin in the incubated generated unknown radioimmunoassay reaction mixture, whereby unbound angiotensin I is adsorbed on the resin strip; and
  removing the resin strip bearing unbound angiotensin I from the reaction mixture.

14. A method as set forth in claim 13 wherein the relative proportions of bound and unbound labeled angiotensin I in said incubated reaction mixture are determined by precounting the reaction mixture prior to immersion of the resin strip therein and postcounting the reaction mixture after removal of the resin strip.

15. A method as set forth in claim 1 wherein said unknown generation sample is incubated at a temperature between about 10°C. and about 60°C.

16. A method as set forth in claim 15 wherein said unknown generation sample is incubated at a temperature of between about 35°C. and about 50°C.

17. A method as set forth in claim 16 wherein said unknown generation sample is incubated at a temperature of approximately 37°C.

18. A method as set forth in claim 1 wherein said generation buffer solution has a pH of appoximately 5.5.

19. A method as set forth in claim 18 wherein said generation buffer solution comprises a buffer selected from the group consisting of potassium acid phthalate and 2,2-dimethyl glutaric acid.

20. A method as set forth in claim 1 wherein said inhibitor is selected from the group consisting of 8-hydroxyquinoline and 2,3-dimercaptopropanol.

21. A method as set forth in claim 1 wherein a nongenerated base sample containing the unknown plasma is mixed with a predetermined amount of radioactively labeled angiotensin I, a predetermined amount of an antibody for angiotensin I, and a sufficient amount of assay buffer solution to provide a base unknown radioimmunoassay reacion mixture containing substantially the same proportions of unknown plasma, labeled angiotensin I, and antibody as said generated unknown radioimmunoassay reaction mixture, said base unknown radioimmunoassay reaction mixture is incubated at the same temperature and for the same time as the generated unknown radioimmunoassay reaction mixture, unbound angiotensin I and bound angiotensin I contained in the base reaction mixture are separated, the relative proportions of bound and unbound labeled angiotensin I in the base reaction mixture are determined, and the angiotensin I content of the base unknown reaction mixture is determined by comparison of the relative proportions of bound and unbound labeled angiotensin I in said base reaction mixture with the relative proportions of bound and unbound labeled angiotensin I in standard radioimmunoassay reaction mixtures containing known amounts of unlabled angiotensin I.

22. A method as set forth in claim 21 wherein said base unknown plasma sample comprising a base aliquot of inhibited plasma and said generation buffer solution is diluted with a reaction medium comprising said assay buffer solution and said labeled angiotensin I to provide a base prereaction mixture, said base prereaction mixture is maintained at a temperature not substantially higher than about 37°C. during the incubation of said unknown generation sample, a base unknown radioimmunoassay reaction mixture is thereafter provided by adding said antibody to said base prereaction mixture, and the radioimmunoassay reaction is carried out by incubating said base reaction mixture at the same time and under conditions identical to those used for the incubation of the generated unknown to radioimmunoassay reaction mixture.

23. A radioimmunoassay method for the in vitro determination of the renin activity of an unknown plasma sample, comprising the steps of:

mixing said plasma sample with an inhibiting solution containing an inhibitor selected from the group consisting of 8-hydroxyquinoline and 2,3-dimercaptopropanol;

providing an unknown generation sample by mixing the unknown plasma sample containing said inhibitor with a generation buffer solution comprising a buffer selected from the group consisting of potassium acid phthalate and 2,2-dimethyl glutaric acid;

providing a base unknown sample having the same composition as said unknown generation sample;

providing a base unknown prereaction mixture by mixing said base unknown sample with a predetermined amount of $^{125}$I labeled angiotensin I, and an amount of an assay buffer solution sufficient to provide in said base unknown reaction mixture a renin concentration no greater than about 1/10 the concentration of renin in said plasma sample;

incubating said unknown generation sample to generate angiotensin I by action of renin upon angiotensinogen, thereby producing a generated unknown plasma sample;

maintaining said base unknown prereaction mixture at a temperature not substantially higher than about 37°C. during the incubation of said unknown generation sample;

providing a generated unknown radioimmunoassay reaction mixture by mixing said generated unknown sample with a predetermined amount of $^{125}$I labeled angiotensin I, a predetermined amount of an antibody for angiotensin I, and an amount of an assay buffer solution sufficient to provide in said generated unknown reaction mixture a renin concentration no greater than about 1/10 the concentration of renin in said plasma sample;

providing a base unknown radioimmunoassay reaction mixture by mixing said base prereaction mixture with a predetermined amount of an antibody for angiotensin I;

incubating both the base unknown radioimmunoassay reaction mixture and the generated unknown radioimmunoassay reaction mixture at a temperature of approximately 37°C. so that a competitive binding reaction takes place between the antibody and both labeled and unlabeled angiotensin I in each of the reaction mixtures;

incubating each reaction mixture in contact with a relatively thin strip of a membrane consisting essentially of an ion exchange resin strip to effect adsorption of unbound angiotensin I on said resin strip;

removing the resin strip from each of said reaction mixtures to effect separation of unbound angiontensin I from bound angiotensin I;

counting radioactivity to determine what proportions of the labeled angiotensin I initially contained in each of said reaction mixtures is bound and what proportion is unbound;

determining the angiotensin I content in both the generated unknown reaction mixture and the base unknown reaction mixture by comparison of the relative proportions of bound and unbound labeled angiotensin I in each of said reaction mixtures with the relative proportions of bound and unbound labeled angiotensin I in standard radioimmunoassay reaction mixtures containing known amounts of unlabeled angiotensin I; and determining the renin activity of the plasma from the difference between the angiotensin I content of the generated unknown reaction mixture and the angiotensin I content of the base unknown reaction mixture.

24. A method as set forth in claim 23 wherein the relative proportions of bound and unbound labeled angiotensin I in said reaction mixtures are determined by precounting the reaction mixtures prior to immersion of the resin strips therein and postcounting the reaction mixtures after removal of the resin strip.

* * * * *

UNITED STATES PATENT OFFICE
CERTIFICATE OF CORRECTION

PATENT NO. : 3,966,896
DATED : June 29, 1976
INVENTOR(S) : Joel Glovsky and James L. Brown It is certified that error appears in the above—identified patent and that said Letters Patent are hereby corrected as shown below:

Column 1, line 16, "in in the" should read -- in the --.
Column 2, lines 30-31, "formative" should read -- formation --.
Column 8, line 4, "lid" should read -- lip --. Column 10, lines 41-42, "preparation" should read -- prereaction --. Column 12, line 60, "mixture" should read -- mixtures --. Column 15, Table XI, under the heading "% Bound" the percentages "4271, 4181 and 4177" should read -- 42.71, 41.81 and 41.77 --.
Column 15, line 39, "supernatent" should read -- supernatant --.
Column 17, line 40, "mixture" should read -- mixtures --.
Column 18, line 64, "reacion" should read -- reaction --. Column 19, line 30, "unknown to" should read -- unknown --.

Signed and Sealed this

First Day of March 1977

[SEAL]

Attest:

RUTH C. MASON
Attesting Officer

C. MARSHALL DANN
Commissioner of Patents and Trademarks